(12) United States Patent
Yager

(10) Patent No.: US 7,125,380 B2
(45) Date of Patent: Oct. 24, 2006

(54) CLAMPING APPARATUS AND METHODS

(75) Inventor: David Yager, Monroe, WA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 213 days.

(21) Appl. No.: 10/383,968

(22) Filed: Mar. 7, 2003

(65) Prior Publication Data

US 2003/0199738 A1    Oct. 23, 2003

Related U.S. Application Data

(63) Continuation-in-part of application No. 09/923,891, filed on Aug. 7, 2001, now Pat. No. 6,949,105, which is a continuation-in-part of application No. 09/783,860, filed on Feb. 13, 2001, now abandoned, which is a continuation-in-part of application No. 09/783,910, filed on Feb. 13, 2001, now abandoned.

(51) Int. Cl.
*A61B 1/32*    (2006.01)
*B25G 3/36*    (2006.01)

(52) U.S. Cl. ............... 600/227; 600/228; 600/231; 403/391

(58) Field of Classification Search ............ 600/227, 600/231, 228, 234, 232; 403/374.1, DIG. 8, 403/391, 389, 384; 24/67.1; 269/45
See application file for complete search history.

(56) References Cited

U.S. PATENT DOCUMENTS

| | | | |
|---|---|---|---|
| 1,858,284 A * | 5/1932 | Schwartz | ............... 403/12 |
| 2,677,369 A | 5/1954 | Knowles | |
| 3,486,505 A | 12/1969 | Morrison | |
| 3,574,374 A | 4/1971 | Keller et al. | |
| 3,875,595 A | 4/1975 | Froning | |
| 3,876,728 A | 4/1975 | Stubstad | |
| 4,023,572 A | 5/1977 | Weigand et al. | |
| 4,116,200 A | 9/1978 | Braun et al. | |
| 4,179,810 A | 12/1979 | Kirsch | |
| 4,309,777 A | 1/1982 | Patil | |
| 4,349,921 A | 9/1982 | Kuntz | |
| 4,461,284 A * | 7/1984 | Fackler | ............... 600/228 |
| 4,599,086 A | 7/1986 | Doty | |
| 4,617,916 A * | 10/1986 | LeVahn et al. | ............. 600/228 |
| 4,645,507 A | 2/1987 | Engelbrecht et al. | |
| 4,714,469 A | 12/1987 | Kenna | |
| 4,743,256 A | 5/1988 | Brantigan | |
| 4,757,983 A | 7/1988 | Ray et al. | |
| 4,759,766 A | 7/1988 | Buettner-Janz et al. | |
| 4,759,769 A | 7/1988 | Hedman et al. | |
| 4,766,328 A | 8/1988 | Yang | |
| 4,777,942 A | 10/1988 | Frey et al. | |
| 4,800,639 A | 1/1989 | Frey et al. | |
| 4,834,757 A | 5/1989 | Brantigan | |
| 4,863,476 A | 9/1989 | Shepperd | |
| 4,863,477 A | 9/1989 | Monson | |
| 4,874,389 A | 10/1989 | Downey | |
| 4,878,915 A | 11/1989 | Brantigan | |
| 4,887,595 A | 12/1989 | Heinig et al. | |

(Continued)

FOREIGN PATENT DOCUMENTS

EP    0 904 741 A2    3/1999

*Primary Examiner*—Pedro Philogene
(74) *Attorney, Agent, or Firm*—Haynes and Boone, LLP

(57) ABSTRACT

The methods and apparatus of this invention provide instrumentation for clamping and securing instruments to support members. Specific embodiments of the invention are particularly useful as devices and methods for use during surgical procedures, such as implantation procedures to properly implant a prosthesis.

12 Claims, 9 Drawing Sheets

U.S. PATENT DOCUMENTS

| | | |
|---|---|---|
| 4,904,260 A | 2/1990 | Ray et al. |
| 4,904,261 A | 2/1990 | Dove et al. |
| 4,908,032 A | 3/1990 | Keller |
| 4,908,036 A | 3/1990 | Link et al. |
| 4,911,718 A | 3/1990 | Lee et al. |
| 4,917,704 A | 4/1990 | Frey et al. |
| 4,932,969 A | 6/1990 | Frey et al. |
| 4,932,975 A | 6/1990 | Main et al. |
| 4,946,378 A | 8/1990 | Hirayama et al. |
| 4,955,908 A | 9/1990 | Frey et al. |
| 4,978,355 A | 12/1990 | Frey et al. |
| 4,997,432 A | 3/1991 | Keller |
| 5,002,576 A | 3/1991 | Fuhrmann et al. |
| 5,015,247 A | 5/1991 | Michelson |
| 5,035,716 A | 7/1991 | Downey |
| 5,047,055 A | 9/1991 | Bao et al. |
| 5,059,193 A | 10/1991 | Kuslich |
| 5,059,194 A | 10/1991 | Michelson |
| 5,242,240 A * | 9/1993 | Gorham ............... 403/391 |
| 5,792,046 A * | 8/1998 | Dobrovolny |
| 5,899,627 A * | 5/1999 | Dobrovolny ............ 403/391 |
| 6,017,306 A * | 1/2000 | Bigliani et al. ........... 600/234 |
| 6,033,363 A * | 3/2000 | Farley et al. ............ 600/234 |
| 6,616,664 B1 * | 9/2003 | Walulik et al. ........... 606/57 |

* cited by examiner

CLAMPING APPARATUS AND METHODS

This application is a continuation-in-part of U.S. patent application Ser. No. 09/923,891, filed on Aug. 7, 2001, now U.S. Pat. No. 6,949,105, having the title "Improved Method and Apparatus for Stereotactic Implantation," which is a continuation-in-part of U.S. patent application Ser. No. 09/783,860, filed on Feb. 13, 2001 now abandoned, having the title "Method and Apparatus for Stereotactic Implantation," and a continuation-in-part of U.S. patent application Ser. No. 09/783,910, filed on Feb. 13, 2001 now abandoned, having the title "Implantable Joint Prosthesis," both of which claim benefit under 35, U.S.C. § 119(e) of Provisional U.S. Ser. No. 60/223,863, filed Aug. 8, 2000, and entitled "Instrumentation and Method for Implanting a Prosthetic Intervertebral Body" and of Provisional U.S. Ser. No. 60/265,218 entitled "Gravity Assisted Localization System," filed Jan. 31, 2001, all of which are hereby incorporated herein by this reference.

FIELD OF THE INVENTION

The invention relates to methods and associated instrumentation for clamping and securing instruments to support members. Specific embodiments of the invention are particularly useful as devices and methods for use during surgical procedures, such as implantation procedures to properly implant a prosthesis.

BACKGROUND OF THE INVENTION

There are many instances when it is necessary, during surgery or otherwise, to attach instruments to a frame or support member. For example, during stereotactic surgery, which involves positioning a stable reference point with respect to a patient in order to properly guide and reference instruments to the surgical site, a support member is mounted with respect to a patient, and surgical instruments are positioned with respect to the support member. This invention seeks to provide such a system with a clamp that allows the stable securing of such instruments.

Obtaining clear access to a surgical site during any open surgical procedure presents certain challenges. These challenges are multiplied when the surgical procedure involves precisely locating a specific target location, such as during stereotactic surgery. There is a need for a system that allows retraction of the patient's tissue in order to allow clear access to the site.

The proper location of an endoprosthetic implant is a key element to the success of the implantation procedure in improving patient quality of life. For example, properly locating an intervertebral endoprosthesis ensures, among other benefits, that the patient will enjoy the full range of motion offered by the implant and will avoid potentially dangerous conditions resulting from contact of the implant with delicate spinal cord structures.

The use of intervertebral implants (arthroplasty) has, in recent years, attained increasing acceptance as a preferable alternative to spinal fusion (arthrodesis) as a method for treating patients where discectomy is indicated. This is in part due to recent advances in implant technology, and in part due to the increasing appreciation of the advantages provided by implantation, including increased range of motion, decreased post-operative damage to adjacent intervertebral discs (which can result from the decreased range of motion at the level of the fusion), decreased risk of harvest site morbidity, etc. This increasing acceptance seems likely to continue for the foreseeable future, and more and more implantation procedures will likely be performed.

Similar considerations apply in other areas of surgery, and in particular, in neurosurgery. For example, during surgery on the brain, the surgeon often anchors a frame to the sides of the patient's head, which provides constant reference points during surgery, irrespective of how the patient's head or neck is positioned or moved during the procedure. This level of stereotactic precision in location and placement is particularly desirable for medical and surgical procedures where the margin for error is very small due to the proximity to the spinal cord and other neuro and vascular structures. However, contrary to brain surgery, in most procedures used for spinal surgery, as well as surgery to other body parts, it is difficult to secure an external frame to the patient's skeleton or soft tissues to provide constant reference points.

Electronic systems exist for stereotactic positioning of medical instruments during surgical procedures. However, these systems are extremely expensive, require significant computing power, are highly complex, require specialized software, and are not always available, particularly in smaller health care systems or in less developed countries.

Accordingly, there remains a need in the art for methods and apparatus for locating, and preferably stereotactically locating, targeted implantation positions, for precisely positioning tools for preparing the implantation site, and for precisely inserting the implant in the desired position that is simple, safe, that does not require expensive electronic or computerized tracking of medical instrumentation, and that can be used with conventionally available imaging technologies. Furthermore, there is a need in the art to provide methods and instrumentation that will allow a surgeon to revise two fused vertebra and interpose an articulating implant therebetween.

While current methods may be sufficient to achieve a successful intervertebral implantation, there remains a need for improved techniques and instruments that provide even more precise localization, such as improved stereotactic location of the desired site of the implant, the precision positioning of milling, burring, and other tools and instruments for conducting the procedure, and the implantation of the endoprosthesis into the prepared site.

There remains a further need for a clamping apparatus and method to assist a practitioner in exposing and preparing a cavity to receive an endoprosthesis or any other surgical implant or treatment. In particular, there is a need for a clamp adapted to secure surgical instruments to a stable support frame for the preparation of a surgical site.

SUMMARY OF THE INVENTION

The methods and apparatus of the invention help to satisfy this need by providing a unique clamp structure that is adapted to help position surgical instruments, such as retractor blades and so forth, in order to expose a surgical site intended to receive an implant. There are numerous ways to describe and characterize the techniques intended to be used in connection with the apparatus and methods of this invention. Exemplary techniques and instrumentation are outlined in U.S. patent application Ser. No. 09/923,891, which provides background and context for the clamps and methods of this invention.

It should be understood, however, that although the clamps and methods described herein are of particular use in connection with surgical instrument stabilization, they may be used in connection with any situation or need that requires stabilization of an instrument or item with respect to a particular site using a support member. For example, the methods of this invention may be used in connection with a workbench for holding tools, a holder for securing writing utensils to a particular surface, clamps for a makeup application professional, and so forth.

Referring back to stereotactic surgical uses, during surgery, once the patient is immobilized in an appropriate position, it is necessary to provide a structure that can act as a reference point. For example, certain embodiments of this invention are intended for use with a surgical frame that can be attached to an operating table and placed such that it defines the surgical site. A temporary machining jig or scaffold for precisely locating various instruments used to prepare the surgical site and for guiding the instruments to the surgical site may be positioned with respect to the surgical frame and the patient.

In order to place such a temporary structure and to appropriately and fully expose the surgical site, it is necessary to retract a patient's skin, muscle tissue or any other tissues that cover and protect the internal surgical site. It is preferable to use the surgical frame to position and support such retraction instruments. Accordingly, various embodiments of the clamps provided by this invention are adapted to position surgical instruments with respect to the surgical frame.

For example, one embodiment of a clamp of this invention comprises a clamp with
(a) a main body comprising (i) a top portion, (ii) a middle portion, and (iii) a base portion, wherein the portions are separated by at least two channels, the clamp further comprising (iv) a cooperating interface adapted to cooperate with at least a portion of the support member;
(b) an instrument holder supported by the main body and defining a receiving aperture adapted to receive and secure an instrument with respect to the clamp; and
(c) a tightening member supported by the main body and adapted to extend through the main body and in use to at least partially compress the at least two channels of the main body such that the instrument holder is secured in at least partial non-rotational and at least partial non-translational stability with respect to the main body and the cooperating interface secures the clamp to at least a portion of the support member.

In another embodiment, the clamp includes:
(a) a main body defining a top portion, a middle portion, and a base portion wherein the top portion and the middle portion are separated by a first channel and the middle portion and the base portion separated by a second channel;
(b) an instrument holder aperture defined by the top portion and the middle portion;
(c) a cooperating interface adapted to cooperate with the support member defined by the middle portion and the base portion;
(d) a throughpin receiving aperture extending through each portion of the main body; and
(e) a throughpin adapted to be inserted through the throughpin receiving aperture, such that upon tightening of the throughpin, the first and second channels are at least partially compressed together.

BRIEF DESCRIPTION OF THE DRAWINGS

FIG. 7 shows generally rail extensions, vertical rods, and rod clamps which facilitate attachment of frame to an operating room table or other structure.

DETAILED DESCRIPTION

Figure 1:
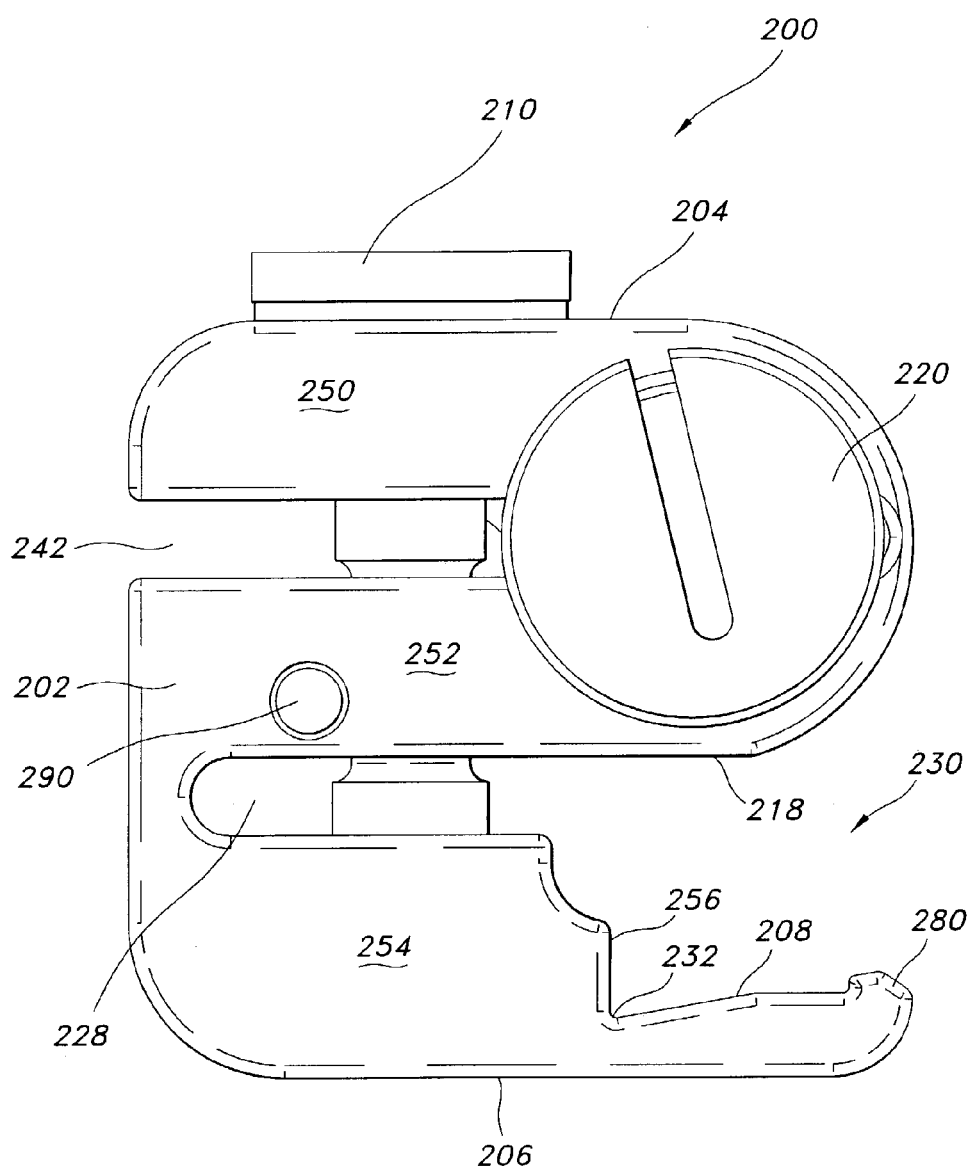
FIG. 1 is a side view of another embodiment of a clamp, showing generally the main body, instrument holder, and cooperating interface.

It will be understood from the description above that the apparatus and techniques of this invention are applicable to a wide variety of procedures, particularly surgical procedures, where precise positioning of an instrument is required. Aspects of the invention are also applicable to any instance in which it is desired to secure any instrument to a support frame or support surface in order to stabilize the instrument with respect to the frame or any reference point relating to the frame.

The description that follows focuses on one embodiment of the invention—the exposure of the intervertebral space and the implantation of an intervertebral endoprosthesis, and in particular, to the implantation of such an endoprosthesis in the intervertebral space between cervical vertebrae using an anterior approach. Those of ordinary skill in the art will recognize that the procedure described below can be varied or modified to be applicable to other spinal implants such as fusion implants or to other approaches, or to lumbar or thoracic vertebral implants, to implants in other parts of the body, such as hips, knees, elbows, or other joints, and to other procedures that do not involve implantation or surgical procedures, but in which instruments need to be positioned with respect to a stable support member.

I. Brief Overview of Procedure

The primary goals and steps of a spinal surgical procedure will be described in order to provide context for the clamps and methods of the present invention. One main goal of any surgery is to provide a precisely formed cavity of predetermined geometry at a precise location, whether it be the site intended to receive an implant, the site to be irrigated, the site to excised, and so forth. In one embodiment, this cavity can then be used to implant a joint prosthesis to restore proper functioning of the joint and/or alleviate pain in the vicinity of the joint. The geometry of the cavity closely approximates the geometry of the implant, and thereby serves to keep the implant in a given position.

However, before the target disc space can be distracted or the additional positioning instruments can be used to prepare the site for receipt of the implant (or other surgical technique that may be necessary), the site must be properly exposed. There are many ways to use the clamps of the present invention in order to assist in achieving appropriate exposure of the site. One particularly useful embodiment includes a clamp positioned on a surgical frame support member that is precisely positioned with respect to the patient. The clamps of the present invention are adapted to cooperate with instruments that the practitioner wishes to secure with respect to the patient by securing the instruments to the frame. In use, the clamps both (a) receive an instrument to be secured, and (b) clamp tightly to the surgical frame support member.

In certain embodiments, the clamps cooperate with retractors to retract patient tissue from the surgical site and to attach, or otherwise associate, the retractors with the surgical frame support member.

II. Placement of Patient and Support Member

Figure 5:
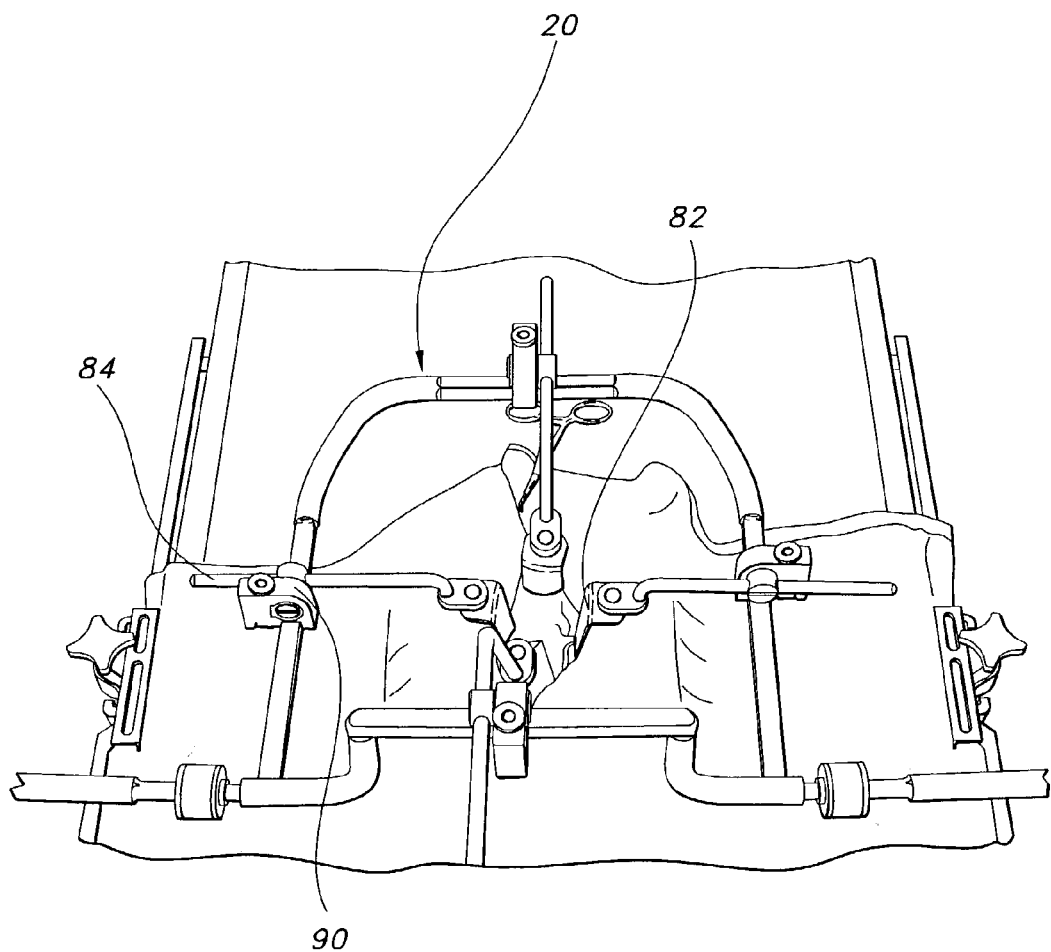
FIG. 5 is a top perspective view of a frame assembly, clamps, retractor blades and retractor blade holders in accordance with one embodiment of the present invention, and illustrates how these components are attached to one another for use during a surgical procedure.
Figure 6:
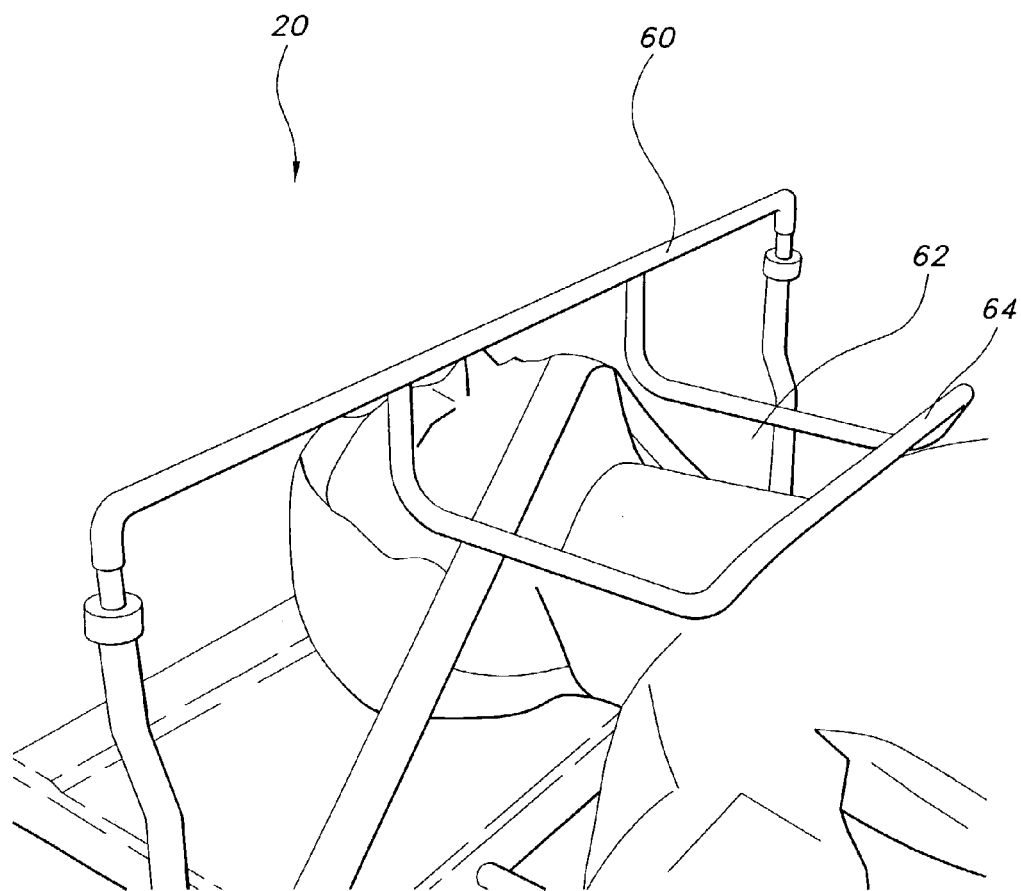
FIG. 6 is a side perspective view of a surgical frame support member positioned relative to a patient.

FIG. 5 shows one embodiment of a surgical frame support member 20 mounted with respect to a patient, and clamps 90 used to support instruments 84 with respect to support member 20 (also referred to as "frame"). FIG. 6 shows a patient's head and/or upper body immobilized on a table or other operating surface with frame 20 positioned with respect thereto.

If the surgery is a spinal surgery, the patient is positioned as shown in FIG. 6 so that the portion of the spine to be implanted has a lordotic angle similar to the patient's neutral position, and so that the spinous processes are midway between the facets (as determined, e.g., by an anterior-posterior radiograph). If the surgery is to be brain surgery, hip, knee, or any other joint surgery, the patient is positioned appropriately for such surgery.

Because this invention is particularly useful in connection with stereotactic surgery or any other surgery that uses an external frame for locating reference points within the brain, spinal cord, etc., the invention will be described as used with a frame for providing such reference points. The frame typically provides an external, three-dimensional frame of reference.

A rigid frame, such a surgical frame support member 20 or an external frame, referred to generally as "support member," is mounted to an operating table or surface to provide reference points during surgery and to secure retractors and other surgical instruments to be used during the procedure. The position of the patient's head and neck (or other anatomy on which is being operated) remains constant with respect to the mounted frame 20. The frame could be secured to any surface that will remain stable during the surgery. As an example, in a particular embodiment described in more detail below, this can be done by attaching an adjustable frame assembly to the side rails of an operating table as shown in FIG. 5. The surgical instruments can then be secured to the frame and stabilized relative to the patient.

Figure 7:
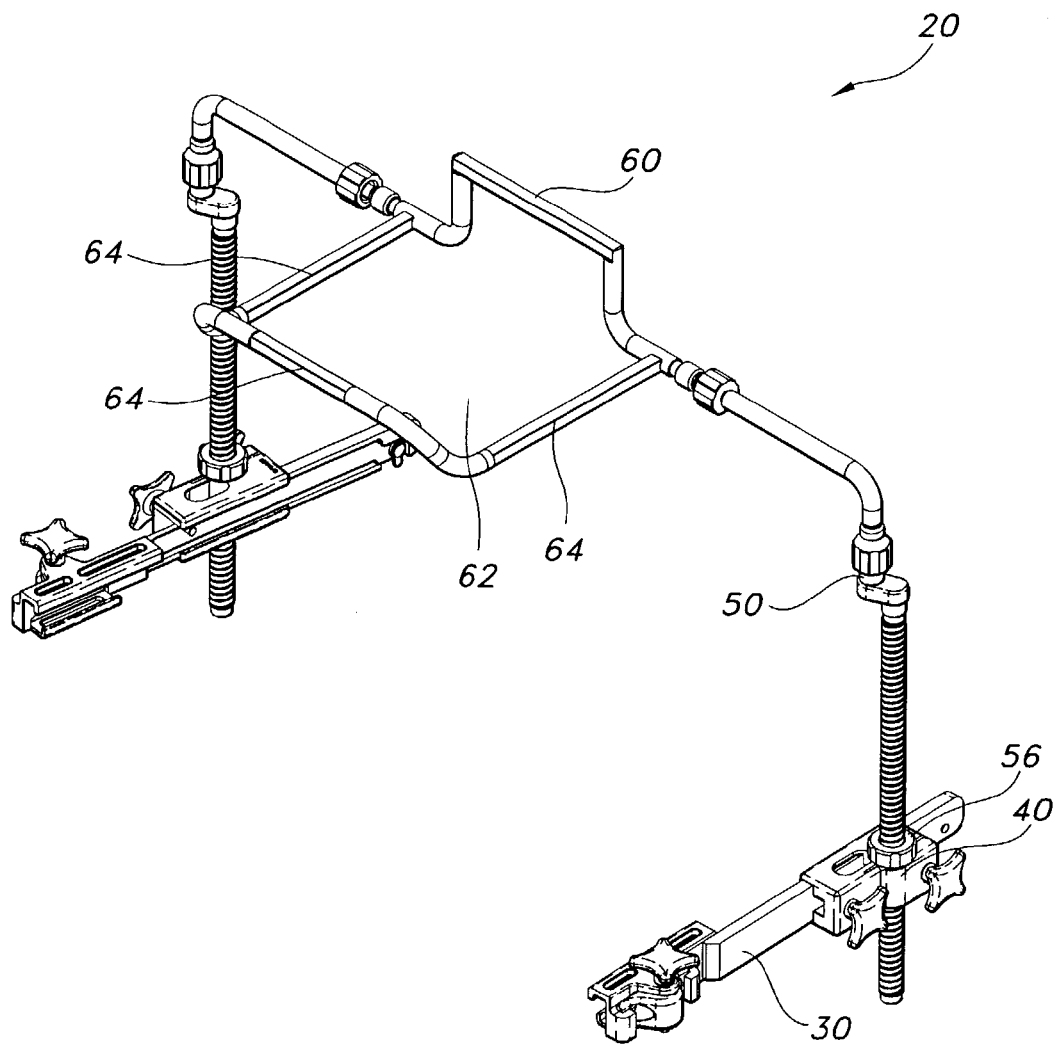
FIG. 7 is a perspective view of a rigid frame support member for use with the various clamps of this invention.

For example, once the patient is stabilized, prepared, and draped, and the position of the spine has been ascertained, adjustable frame assembly or support member 20 shown completely assembled in FIG. 7 is attached to the operating table. Frame assembly 20 may be a one-piece assembly or may comprise several modular components that can be disassembled and packaged for storage and/or sterilization and then erected during the procedure.

The exemplary embodiment of frame assembly 20 shown in FIG. 7 comprises side rail extensions 30, vertical rod clamps 40, vertical rods (also called vertically extending rods) 50, rod collars 56, and rigid frame support member 60. Standard operating room tables have side rails along the sides, which are used to provide a base for the frame assembly 20. Once frame assembly 20 is erected, each side rail will have a side rail extension 30, vertical rod clamp 40, and vertical rod 50, attached thereto. The vertical rods 50 support the rigid frame 60.

Generally, as illustrated in FIG. 6, rigid frame support member 60 has an aperture 62 that should be positioned approximately over the target surgical space, and relatively close to the patient. Aperture 62 is defined by three or more connecting portions 64, which will ultimately serve as a support for instruments and a reference point during the procedure. Connecting portions 64 optimally collectively form a frame square or rectangle. Connecting portions 64 may specifically be substantially horizontal lateral side portions, a cephalad portion and a caudal portion.

Once assembled, to ensure that the frame assembly 20 is appropriately erected, a centering level may be placed on the rigid frame 60, i.e., on one of the connecting portions 64. The surgeon should then adjust the frame assembly as necessary in order to ensure that the frame is level in the lateral direction by adjusting and tightening the vertical rod collars 56 and vertical rod clamps 40 to raise and/or lower the vertical rods 50.

III. Preparation of Surgical Site

Once the patient and frame assembly have been positioned, the surgeon is ready to begin the procedure. The surgeon prepares the site for the medical procedure. For example, for implantation of a spinal prosthesis, the surgeon prepares the surgical site much as he would for an anterior cervical discectomy (ACD). After the surgeon makes a routine anterior exposure at the target disc level, he/she should confirm that the proper target location is exposed. Confirmation is preferably made by imaging a probe or needle placed adjacent to the target disc, and viewing the probe or needle under fluoroscopy.

After the incision is made, the surgical site is exposed by suitable soft tissue retraction. This retraction is facilitated by retractor blades attached to the frame by various embodiments of the clamp described herein. For example, in the spinal surgery depicted in FIG. 5, the surgeon inserts a retractor blade 82 near the level of the target space in order to retract each of the longus colli muscles, and other soft tissue, such as the trachea. To maintain the retracted position, the surgeon needs to join the retractor blade 82 to a connecting portion 64 of frame assembly 20.

Figure 8:
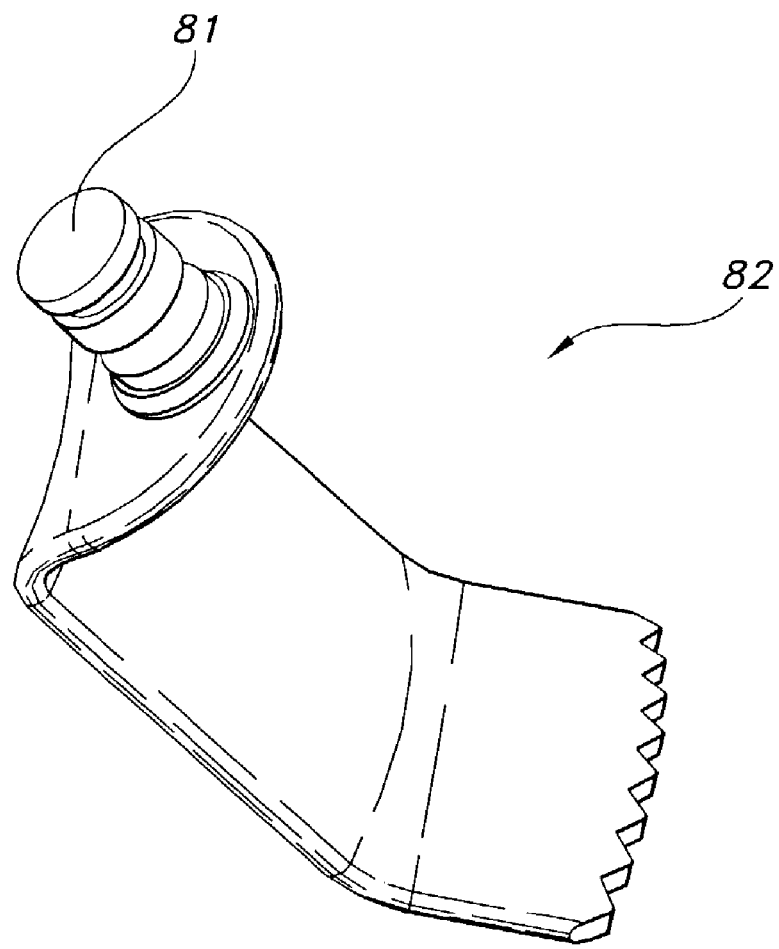
FIG. 8 is a perspective view of one embodiment of a retractor blade of the invention, adapted to interface with a retractor blade holder illustrated in FIG. 9.
Figure 9A:
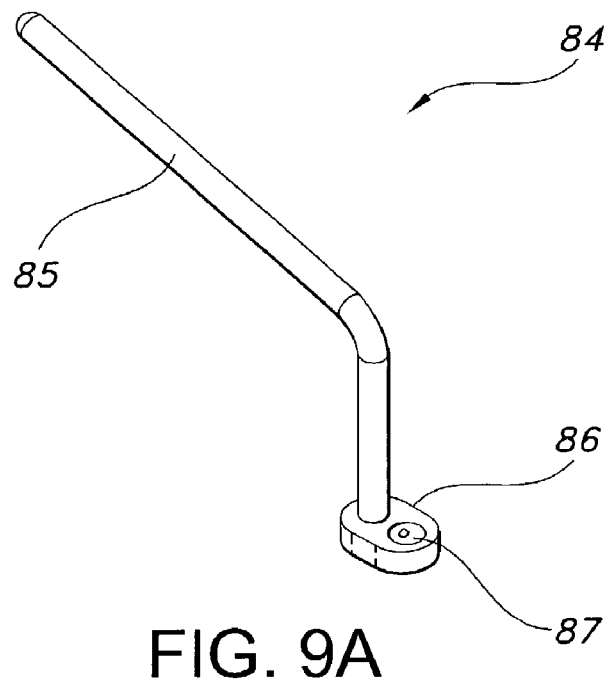
FIG. 9 includes a perspective view (A), a side plan view (B), and a bottom plan view (C) of one embodiment of a retractor blade holder, which is adapted to receive the retractor blade of FIG. 8.
Figure 9B:
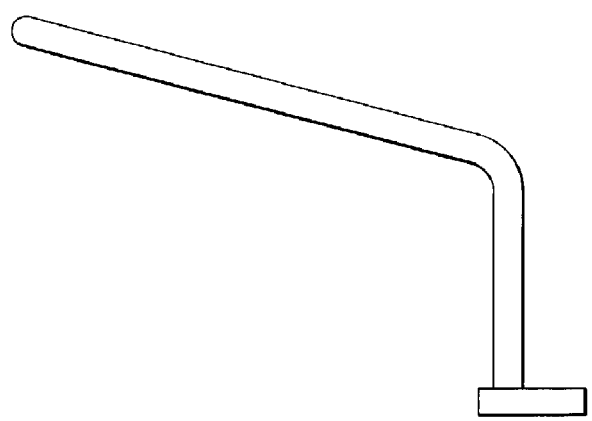
Figure 9C:
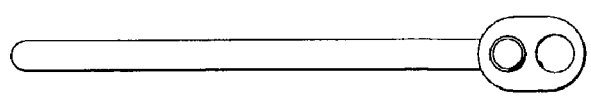

In one embodiment, the surgeon attaches or joins the retractor blade 82, shown in FIG. 8, to the face of a retractor blade holder 84, shown in FIGS. 9A–9C. Retractor blade 82 may be toothed or smooth and is provided in a plurality of shapes and sizes. Retractor blade 82 has a typical retracting portion as well as a connecting portion, such as knob 81. Retractor blade holder 84, shown in FIGS. 9A–C, has a face 86 with a connecting portion, such as aperture 87, which connects to the connecting portion of retractor blade 82, for example, knob 81. Retractor blade holder 84 has handle 85 that may be angled (as shown) or straight (not shown).

IV. Clamp

A clamp is provided that cooperates with the frame assembly and receives an instrument to secure the instrument relative to the frame assembly and the patient. Any type of clamp that provides this function should be considered within the scope of this invention.

As shown in FIG. 5, a clamp 200 may be secured to the frame assembly at the connecting portion 64, and receives an instrument. In FIG. 5, the instrument is shown as a retractor blade holder 84, but it should be understood that any instrument to be clamped to support member can be used as described herein. The purpose of clamp is to stabilize an instrument with respect to the support member, such as frame assembly 20.

A clamp is tightened onto the frame assembly with a hex driver (not shown) so that the clamp is stable and secure. In other words, the clamp is adapted to grip at least a portion of an instrument, such handle 85 of retractor blade holder 84, tightly. Clamp is also adapted to be secured to a support member, such as frame assembly 20, so that the clamp and instrument are maintained in a stationary position with respect to the patient. Since the clamps describers herein simultaneously grip an instrument and the frame assembly 20, it alleviates the need for two separate locking devices.

Figure 2:
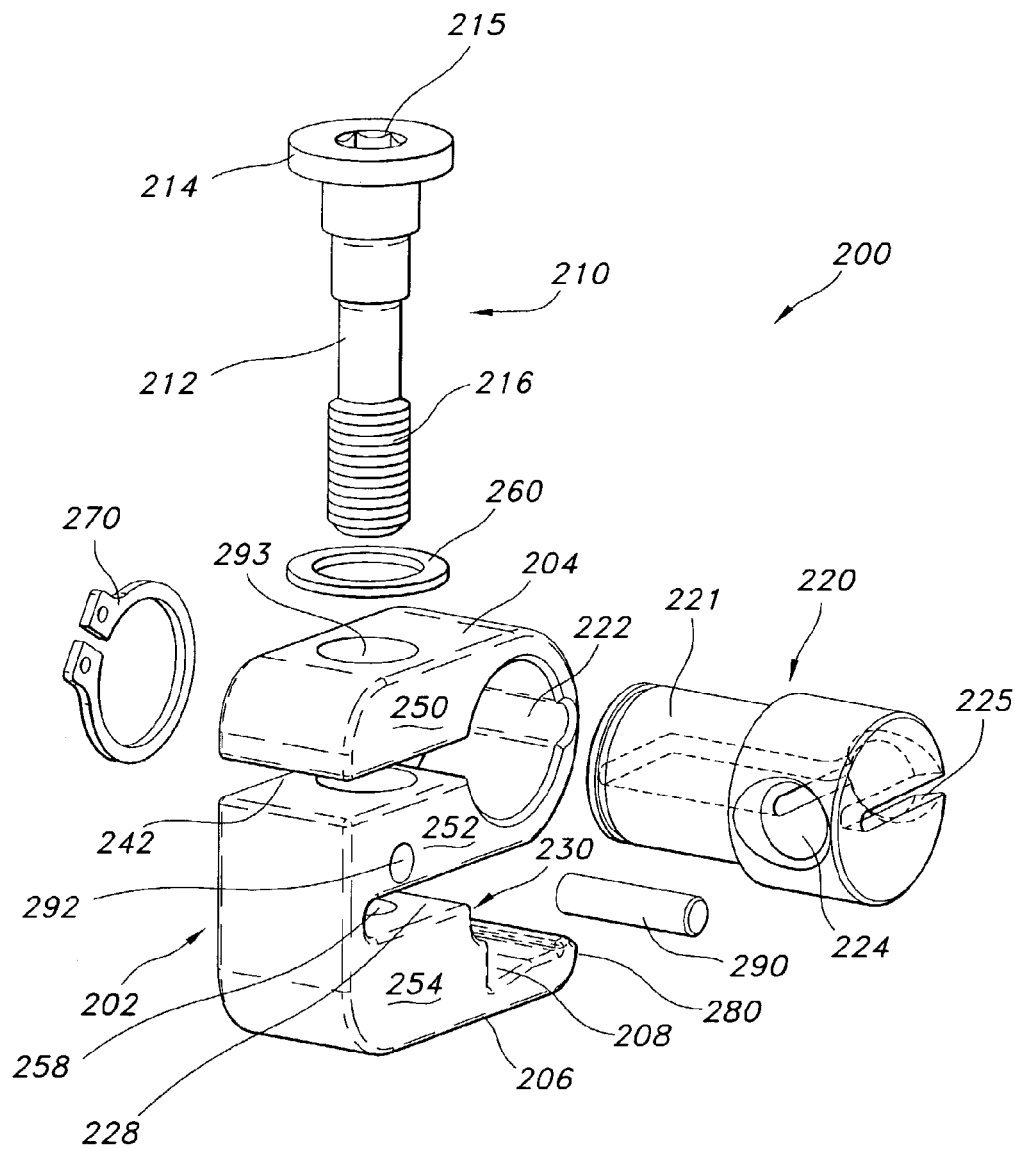
FIG. 2 is an exploded perspective view of the clamp of FIG. 1.

One embodiment of clamp 200, shown in FIGS. 1–2, provides main body 202 with an upper surface 204 and a base 206. Clamp 200 is further provided with an S-type shape design that is divided into top portion 250, middle portion 252, and base portion 254 by channels 228 and 242. When throughpin 210 is tightened, channels 228 and 242 are compressed, tightening main body 202 and drawing top portion 250 and base portion 254 closer to middle portion 252 than when throughpin is not tightened. This accomplishes a number of tightening and securing functions, i.e., tightening clamp 200 to support member 20 while securing an instrument in place.

Main body 202 also features cooperating interface 230, which is adapted to cooperate with and secure clamp 200 onto frame support member. Cooperating interface 230 is preferably defined at least in part by foot 208 of base 206, side 256 of base portion 254, and surface 218 of middle portion 252. Cooperating interface 230 may optionally define deep indent 232, which is adapted to provide a secure grasp to frame assembly and allow sufficient clearance for cooperating interface 230 to receive connecting portion 64 of frame support member 20.

Main body 202 also supports throughpin 210 and instrument holder 220. Throughpin 210, as shown in the exploded view of FIG. 2, is a bolt having a straight portion 212 and a head portion 214. Straight portion 212 is preferably threaded at its lower portion 216 to facilitate connection with aperture 258 of base portion 254. Throughpin 210 may optionally be associated with washer 260 that protects the interface between the head portion 214 and main body 202. In use, throughpin 210 extends through an aperture 293 of top portion 250 (aperture 293 also extends through middle portion 252 of main body 202) and cooperates with aperture 258 of base portion 254.

Top portion 250 and middle portion 252 at least partially further define aperture 222, and instrument holder 220 is adapted to be received by aperture 222. Aperture 222 is preferably circular in shape to allow rotation of instrument holder 220 therein, but it should be understood that aperture 222 and corresponding shaft 221 of instrument holder 220 may be any shape, such as square, octagonal, star-shaped (such that splines on the shaft 221 interface with slots in aperture 222), and so forth.

Instrument holder 220 has an receiving aperture 224 adapted to receive surgical instruments that the surgeon desires to secure to the frame, for example, retractor blade holder 84. Instrument holder 220 is rotatably positioned within aperture 222 and is secured by retaining ring 270. Optimally, instrument holder 220 swivels in aperture 222 to provide a proper angle of the opening receiving aperture 224 with respect to the instrument, such as handle 85 of a retractor blade holder 84. Tightening the throughpin 210 causes the sides defining channels 242 and 228 to compress, causing the internal surfaces of top 250 and middle 252 portions adjacent aperture 222 to press against and immobilize instrument holder 220 with respect to the clamp main body 202. (This compression also causes internal surfaces of middle portion 252 and base portion 254 to press against a support member if clamp 200 is associated therewith, allowing cooperating interface 230 to cooperate with a connecting portion 64 and secure clamp 200 thereto.)

Instrument holder 220 also features slot 225 that extends from receiving aperture 224 to an exterior surface of instrument holder 220. As the internal surfaces adjacent aperture 222 press against instrument holder 220, the sides defining slot 225 are also compressed, thereby compressing the sides of receiving aperture 224 onto any instrument inserted therein. This prevents substantial translational or rotational motion of the instrument within receiving aperture 224. In other words, when the throughpin 210 is rotated in one direction, its threads engage aperture 258 of base portion 254 and urge internal surfaces of top portion 250 and middle portion 252 against shaft 221 of instrument holder 220, simultaneously compressing channel 242 and constricting the aperture 222, which in turn compresses slot 225 and constricts the receiving aperture 224 of the instrument holder 220.

For example, in use, when throughpin 210 is tightened, portions 250, 252, and 254 are drawn closer together by the tightening of throughpin 210 as threads of lower portion 216 are received by threads of aperture 258 of base portion 254. This tightening secures instrument holder 220 in place because aperture 222 (into which shaft 221 of instrument holder 220 is inserted) is made smaller by the drawing together of top portion 250 and middle portion 252.

Additionally, cooperating interface 230 is tightened by the drawing together of middle portion 252 and base portion 254. When cooperating interface 230 abuts a support member, such as frame 20, it cooperates with and secures clamp 200 to rigid frame.

This tightening of throughpin 210 is preferably conducted once handle 85 of retractor blade holder 84 has been placed through receiving aperture 224 of instrument holder 220 and as cooperating interface 230 is in a position to receive or abut at least a portion of support member. The tightening and bringing together of top portion 250, middle portion 252, and base portion 254 simultaneously secures instrument holder 220 in at least partial non-rotational and non-translatable configuration (or at least in rotational and translational stability with respect to main body 202) while securing clamp 200 in at least partial non-rotational and non-translational configuration (or at least in rotational and translational stability) with respect to support member.

To tighten clamp 200 and drive the throughpin 210 into aperture 258, a clamp hex driver (not shown) engages head portion 214 of throughpin 210. Head portion 214 has a hexagonal opening 215 corresponding to a pattern on hex driver. Alternatively, head portion 214 may have any configuration adapted to correspond to an associated driver.

In general, throughpin 210 can be tightened just enough to secure cooperating interface 230 with frame. This will cause the surface 218 of middle portion 252 and foot 208 of base portion 206 to abut connecting portion 64 of frame, thereby securing clamp 200 to frame.

Clamp 200 may also optionally feature securing pin 290. In use, securing pin 290 is received by securing pin aperture 292 and interacts with threads on lower portion 216 of throughpin 210 to prevent throughpin 210 from becoming disengaged from main body 202. For example, clamp 200 is preferably provided to the practitioner in the assembled state shown in FIG. 1. Securing pin 290 is preferably non-removably attached in securing pin aperture 292.

In one embodiment, lower portion 216 has a diameter slightly larger than the diameter of straight portion 212. Once the upper threads of throughpin 210 engage securing pin 290, throughpin 210 can no longer rotate to remove pin 210. For example, if throughpin 210 is rotated clockwise to be inserted through main body 202 and rotated counterclockwise for removal, once upper threads reach securing pin 290, throughpin can no longer be turned counterclockwise and thus cannot be removed, preventing throughpin 210 from becoming disengaged from main body 202. This optional securing pin feature prevents the practitioner from having to locate loose parts in the operating room during surgery.

Another optional feature for clamp 200 is lip 280 on foot of base 208. Lip 280 acts to grasp the support member and provide an additional securing function. It is preferably formed as a slightly curved portion on foot of base 208.

Clamp 200 thus provides a mechanism that will temporarily hold two components (e.g. frame 60 and an instrument, such as retractor blade holder 84) relative to one another, such that they can be repositioned along one or more of three degrees of movement (e.g., (1) translation of instrument along connecting portion 64, (2) translation of instrument within receiving aperture 224, and (3) rotation of instrument relative to frame 20 by rotating instrument holder 220 within aperture 225). Upon obtaining the proper positioning of the two components relative to one another, clamp 200 locks that position along each of the three degrees of movement by actuating a single mechanism, e.g. rotating throughpin 210.

Figure 3:
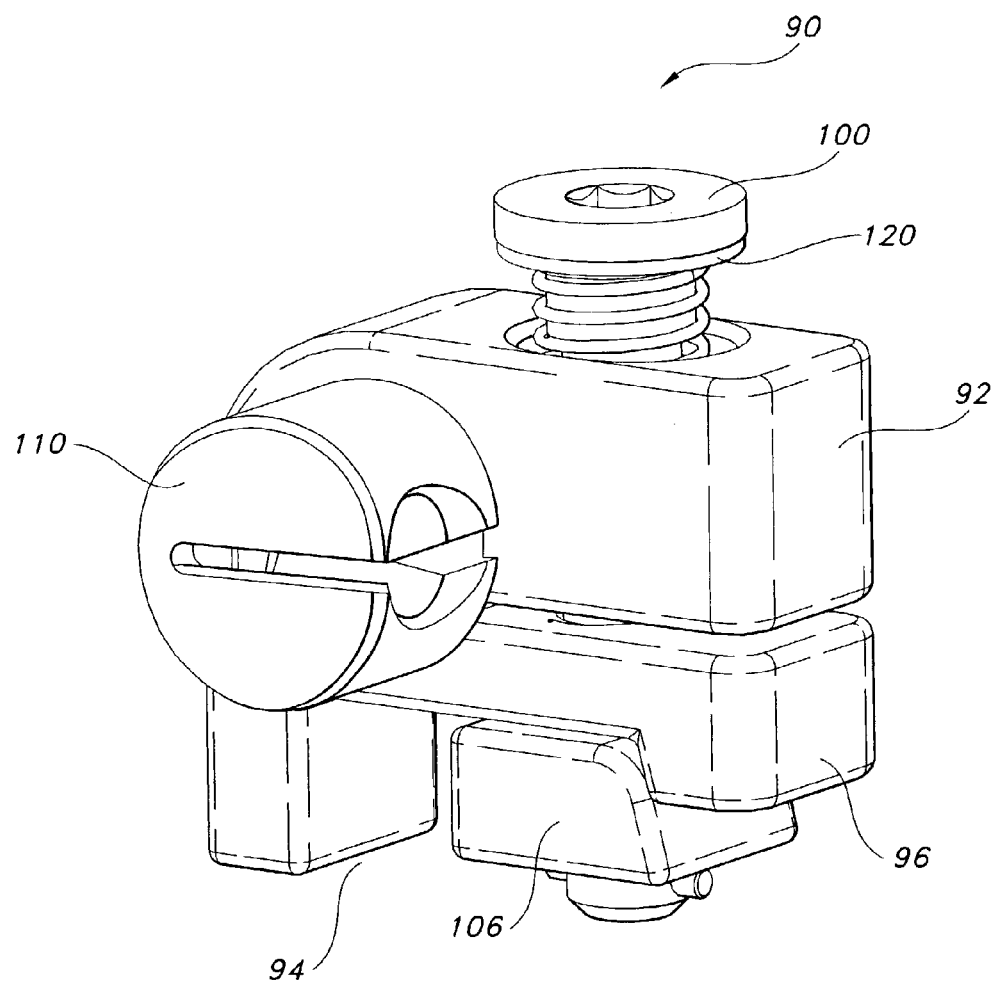
FIG. 3 is a perspective view of one embodiment of a clamp, showing generally a main body, throughpin, securing block, and instrument holder.
Figure 4:
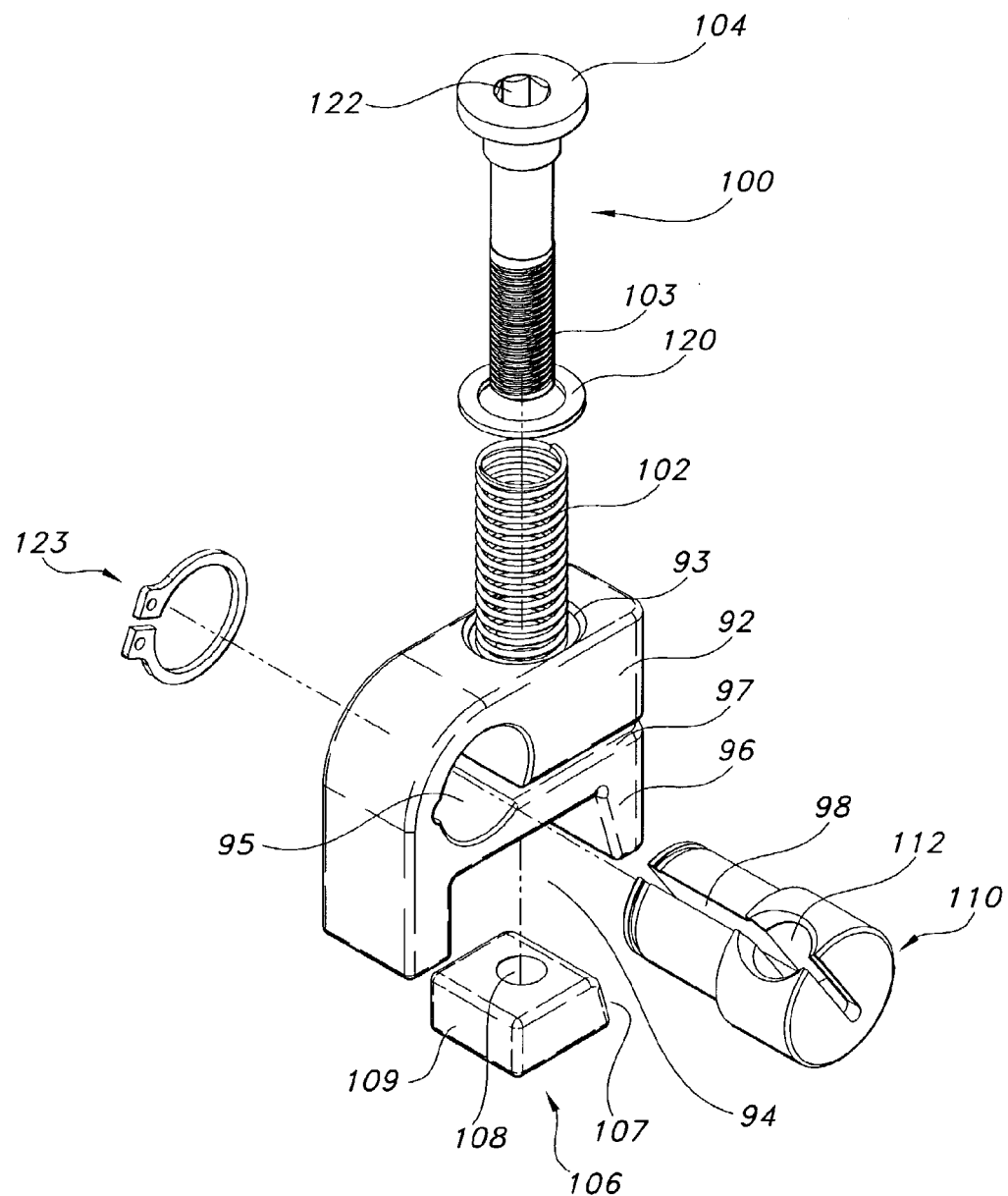
FIG. 4 is an exploded perspective view of the clamp of FIG. 3.

Another specific embodiment of a clamp according to the invention is shown in FIGS. 3–4. Clamp 90 has main body 92 with upper, lower, and lateral sides. Main body 92 supports throughpin 100, securing block 106, and an instrument holder 110. Main body 92, detailed in FIG. 3, has a groove or cut out portion 94 on its lower side that is adapted to cooperate with connecting portions 64 (shown in FIGS. 5 and 6) of the frame assembly 20. Groove 94 is defined by sides, at least one of the sides form from main body foot 96. Main body 92 also features channel 97 extending from an outer surface of main body 92 to an aperture 95 (also called a first aperture) in inner portion of main body 92 separating main body into a first and second portion. Channel 97 in part secures instrument holder 110 in place when clamp 90 is tightened.

Throughpin 100 extends through an aperture 93 in main body 92 and cooperates with securing block 106. Throughpin 100 is a bolt having a straight portion 103 and a head portion 104. Straight portion 103 is preferably threaded at its lower portion to facilitate connection with securing block 106. Throughpin 100 may optionally be associated with washer 120 that protects the interface between the head portion 104 and main body 92. It may also be associated with a spring 102 that biases throughpin 100 upward and facilitates upward movement of the throughpin 100 through aperture 93. In a one embodiment, the spring is a coil spring disposed in the second aperture, and the throughpin passes through the coil spring.

In use, straight threaded portion 103 interfaces and cooperates with securing block 106. Securing block 106 has a threaded bore 108 that receives straight threaded portion 103. Securing block 106 has at least sides 107 and 109. One of those sides (shown here as side 107) may be beveled and corresponds to and interfaces with the main body foot 96. Side 109 is adapted to contact connecting portion 64 of the rigid frame 60.

Securing block 106 fits into groove 94. Particularly, side 107 of securing block 106 fits into and interfaces with main body foot 96. As illustrated, side 107 is beveled and foot 96 has a corresponding bevel. This angle configuration makes clamp 90 less prone to slipping once throughpin 100 is tightened. To tighten the clamp 90 and drive the straight threaded portion 103 into the threaded bore 108, a clamp hex driver (not shown) engages head portion 104 of throughpin 100. Head portion 104 has a hexagonal opening 122 corresponding to a pattern on hex driver, quite similar to a hexagonal head screw driver/screw combination. As the clamp is tightened, the bevel on side 107 moves up the corresponding bevel on foot 96, which causes side 109 to move toward connecting portion 64 of frame assembly 20, securing the clamp to the frame.

Beveled side 107 and spring 102 provide a quick release mechanism for clamp 90. In general, throughpin 100 can be tightened just enough to secure connecting portion 64 of the rigid frame 60 within groove 94. The clamp can then be quickly and easily released from connecting portion 64 by simply pressing down on the biased throughpin 100. Block 106 will move down, and because of beveled surface 107, block 109 will translate toward foot 96 thereby increasing the width of groove 94 and releasing the clamp's lock on frame connecting portion 64. Clamp 90 can then be repositioned along connecting portion 64 and the pressure on the top of throughpin 100 released. This will cause the side 109 to again clamp against connecting portion 64.

Clamp 90 is also provided with an instrument holder 110 that is rotably positioned within aperture 95 and optionally secured by retaining ring 123. Instrument holder 110 has an opening 112 adapted to receive surgical instruments that the surgeon desires to secure to the frame, e.g. retractor blade holder 84. For instance, FIG. 5 shows handle 85 of retractor blade holder slid into and received by holder 110.

Instrument holder 110 swivels to provide a proper angle of the opening 112 with respect to the instrument. Tightening the throughpin 100 causes the sides defining channel 97 to compress as securing block 106 moves upward. This causes the internal surfaces adjacent aperture 95 to press against and immobilize instrument holder 110 with respect to the clamp main body 92, thus securing instrument in place.

Instrument holder 110 also has slot 98 that extends from opening 112 to an exterior surface of instrument holder 110. As the internal surfaces of adjacent aperture 95 press against instrument holder 110, the sides defining slot 98 are compressed, thereby compressing the sides of aperture 112 onto any instrument inserted therein. This prevents any translational motion within slot 112 of the instrument. In other words, when the throughpin 100 is rotated in one direction, its threads urge the securing block 106 against the lower side of the main body 92, simultaneously compressing the channel 97 and constricting the first aperture, which in turn compresses the slot and constricts the opening of the instrument holder, and narrows the support channel.

Clamp 90 thus provides a mechanism that will temporarily hold two components (e.g. frame 60 and instrument, such as retractor blade holder 84) relative to one another, such that they can still be repositioned along one or more of three degrees of movement (e.g., (1) translation of instrument along connecting portion 64, (2) translation of instrument within opening 112, and (3) rotation of instrument relative to frame 60 by rotating instrument holder 110 within aperture 95). Upon obtaining the proper positioning of the two components relative to one another, clamp 90 provides a simple means of locking that position along each of the three degrees of movement by actuating a single mechanism, e.g. rotating throughpin 100.

V. Tissue Retraction and Remainder of Surgery Conducted

Once the retractor blade holder 84 is secured to clamp 90, 200, preferably by sliding handle 85 of the holder 84 into opening 112 or receiving aperture 224, the surgeon joins the retractor blade holder 84 to retractor blade 82. (Note that these steps may be conducted in any order, based upon the surgeon's preference.) The surgeon retracts tissues and muscles and attaches clamp 90, 200 to the rigid frame 60 and secures clamp 90, 200 to both the frame and the retractor blade holder with the hex driver.

These retracting and positioning steps are repeated for the opposite side of the incision, as well as the cephalic and caudal aspects of the incision. This system and method allows the surgeon to create the maximum symmetrical exposure at the target disc space, and free his hands for the surgical procedure. In addition, the rigid frame and clamp system provides a completely rigid retraction system that allows the retraction of both midline and lateral structures, which offer differing resistances to retraction, without movement of the frame relative to the patient.

The remaining surgery may be conducted, whether it is removal of a portion of the target disc, placement or replacement of an implant, delivery of drugs or other agents, excision of a tumor, and so forth. An example of such a procedure is described by U.S. patent application Ser. No. 09/923,891, filed on Aug. 7, 2001, having the title "Improved Method and Apparatus for Stereotactic Implantation" and U.S. patent application Ser. No. 09/783,860, filed on Feb. 13, 2001, having the title "Method and Apparatus for Stereotactic Implantation." An example of a joint prosthesis that can be placed using the clamps of this invention is described by U.S. patent application Ser. No. 09/783,910, filed on Feb. 13, 2001, having the title "Implantable Joint Prosthesis."

The particular embodiments of the invention having been described above are not limiting of the present invention, and those of skill in the art can readily determine that additional embodiments and features of the invention are within the scope of the appended claims and equivalents thereto.

What is claimed is:

1. A clamp for securing an instrument to a support member, the clamp comprising:
   (a) a main body comprising (i) a top portion, (ii) a middle portion, and (iii) a base portion, wherein the porlions are separated by at least two channels, the clamp further comprising (iv) a cooperating interface adapted to cooperate with at least a portion of the support member;
   (b) an instrument holder supported by the main body and defining a receiving aperture adapted to receive and secure an instrument with respect to the clamp, wherein the aperture is defined to have a receiving axis that is generally orthogonal to a long axis of the instrument holder;
   (c) a tightening member supported by the main body and adapted to extend through the main body and in use to at least partially compress the at least two channels of the main body such that an instrument in the instrument holder is secured in at least partial non-rotational and at least partial non-translational stability with respect to the main body and the cooperating interface secures the clamp to at least a portion of the support member.

2. The clamp of claim 1, wherein the tightening member comprises a throughpin adapted to extend through the main body such that when tightened, the throughpin at least partially compresses components of the main body together.

3. The clamp of claim 1, wherein the support member comprises a surgical frame adapted to be positioned with respect to a patient and the instrument holder is adapted to receive medical instruments.

4. The clamp of claim 1, further comprising an instrument interposed in the receiving aperture and wherein the instrument holder further comprises a side slot that at least partially compresses when the tightening member is activated such that the instrument is securely positioned in the receiving aperture when the main body is compressed by the tightening member.

5. A system for positioning and stabilizing surgical instruments, comprising:
   (a) a support member for positioning over a surgical site;
   (b) a clamp for securing instruments to the support member, wherein the clamp comprises:
      (i) a main body comprising a top portion, a middle portion, and a base portion, wherein the portions are separated by at least two channels, the clamp further comprising a cooperating interface adapted to cooperate with at least a portion of the support member;
      (ii) an instrument holder supported by the main body and defining a receiving aperture adapted to receive and secure an instrument with respect to the clamp, wherein the receiving aperture is defined to have a receiving axis that is generally offset to a long axis of the instrument holder;
      (iii) a tightening member supported by the main body and adapted to extend through the main body and in use to at least partially compress the at least two channels of the main body such that an instrument in the instrument holder is secured in at least partial non-rotational and at least partial non-translational stability with respect to the main body and the cooperating interface secures the clamp to at least a portion of the support member; and
   (c) an instrument for being received by the clamp.

6. The system of claim 5, wherein the instrument holder includes a slot extending from the receiving aperture to an exterior surface of the instrument holder.

7. A method for clamping an instrument to a support member, comprising:
   (a) providing a support member;
   (b) providing an instrument;
   (c) providing a clamp, comprising:
      (i) a main body comprising a top portion, a middle portion, and a base portion, wherein the portions are separated by at least two channels, the clamp further comprising a cooperating interface adapted to cooperate with at least a portion of the support member;
      (ii) an instrument holder supported by the main body and defining a receiving aperture adapted to receive and secure an instrument with respect to the clamp, wherein the receiving aperture is defined to have a receiving axis that is generally orthogonal to a long axis of the instrument holder;
      (iii) a tightening member supported by the main body and adapted to extend through the main body and in use to at least partially compress the at least two channels of the main body such that the instrument holder is secured in at least partial non-rotational and at least partial non-translational stability with respect to the main body and the cooperating interface secures the clamp to at least a portion of the support member;

(d) inserting the instrument into the instrument holder;

(e) positioning the cooperating interface such that it cooperates with at least a portion of the support member; and (f) tightening the tightening member to (1) secure the instrument in at least partial non-rotational and at least partial non-translational movement with respect to the clamp and (2) secure the clamp in at least partial non-rotational and at least partial non-translational movement with respect to the support member.

8. The method of claim 7, wherein tightening the tightening member to secure the instrument includes compressing the width of a slot in the instrument holder that extends from the receiving aperture to an exterior surface of the instrument holder.

9. A clamp system comprising:
an integrally formed main body defining a top portion, a middle portion, and a base portion wherein the top and middle portions are at least partially divided by a first channel and the middle and base portions are at least partially divided by a second channel;
an instrument aperture defined by the top portion and the middle portion;
a cooperating portion defined by the middle and base portions and adapted to cooperate with a support member; and
a throughpin adapted for insertion through the top, middle, and base portions such that upon tightening the throughpin, the first and second channels are at least partially compressed; and
an instrument holder extending into the instrument aperture, wherein the instrument holder comprises a slot such that upon tightening the throughpin, the slot is at least partially compressed.

10. The clamp system of claim 9 further wherein the throughpin comprises a threaded portion adapted to engage a threaded aperture in the main body.

11. The clamp system of claim 9 wherein the at least partially compressed channels cause the cooperating portion to clamp to the support member to at least partially secure the clamp with respect to the support member.

12. A method for clamping an instrument to a support member, the method comprising:
providing a support member;
providing an instrument;
providing a clamp comprising:
an integrally formed main body defining a top portion, a middle portion, and a base portion wherein the top and middle portions are at least partially divided by a first channel and the middle and base portions are at least partially divided by a second channel;
an instrument aperture defined by the top portion and the middle portion;
a cooperating portion defined by the middle and base portions and adapted to cooperate with a support member; and
a throughpin adapted for insertion through the top, middle, and base portions such that upon tightening the throughpin, the first and second channels are at least partially compressed;
inserting an instrument holder into the instrument aperture;
inserting the instrument into the instrument holder; placing the cooperating portion in cooperating interface with the support member; and
tightening the throughpin to (a) secure the instrument such that rotational and translational movement of the instrument with respect to the clamp is at least limited and (b) secure the clamp such that rotational and translational movement of the clamp with respect to the support member is at least limited.

* * * * *